United States Patent [19]

Corbin

[11] 4,338,305
[45] Jul. 6, 1982

[54] USE OF LRH AND LRH AGONISTS

[75] Inventor: Alan Corbin, Radnor, Pa.

[73] Assignee: American Home Products Corporation, New York, N.Y.

[21] Appl. No.: 602,152

[22] Filed: Aug. 11, 1975

Related U.S. Application Data

[63] Continuation-in-part of Ser. No. 561,524, Mar. 24, 1975, abandoned, which is a continuation-in-part of Ser. No. 523,302, Nov. 13, 1974, Pat. No. 4,272,432.

[51] Int. Cl.$^3$ .............................................. A61K 37/00
[52] U.S. Cl. ................................................... 424/177
[58] Field of Search ............... 424/177; 260/112.5 LH

[56] References Cited

U.S. PATENT DOCUMENTS

| | | |
|---|---|---|
| 3,813,382 | 5/1974 | McKinley et al. ........ 260/112.5 LH |
| 3,824,227 | 7/1974 | Rees et al. ................. 260/112.5 LH |
| 3,842,065 | 10/1974 | Rees ......................... 260/112.5 LH |
| 3,853,837 | 10/1974 | Fujino et al. ............. 260/112.5 LH |
| 3,888,838 | 6/1975 | Immer et al. ............. 260/112.5 LH |
| 3,914,412 | 10/1975 | Gendrich et al. ......... 260/112.5 LH |
| 3,937,695 | 2/1976 | Sarantakis ................. 260/112.5 LH |
| 4,010,261 | 3/1977 | Johnson et al. ........... 260/112.5 LH |

OTHER PUBLICATIONS

Schally et al.: Am. J. Obstet. Gynecol., 114, 423–442 (1972).

Vilchez–Martinez et al.; Endocrinology, 95, 213–218 (1974).

Primary Examiner—Delbert R. Phillips
Attorney, Agent, or Firm—Richard K. Jackson

[57] ABSTRACT

The use of LRH and LRH agonists as contraceptives in the planetal mammal is disclosed.

24 Claims, No Drawings

USE OF LRH AND LRH AGONISTS

RELATED APPLICATIONS

This application is a continuation-in-part of Ser. No. 561,524, filed Mar. 24, 1975, now abandoned, which application was a continuation-in-part of Ser. No. 523,302 filed Nov. 13, 1974, now U.S. Pat. No. 4,272,432.

BACKGROUND OF THE INVENTION

Luteinizing hormone releasing hormone (LRH) is a known decapeptide presenting the amino acid sequence L-(5-oxo-prolyl)-L-histidyl-L-tryptophyl-L-seryl-L-tyrosyl-glycyl-L-leucyl-L-arginyl-L-prolyl-glycinamide D-Ser group with or without the des-Gly-NH$_2^{10}$ modification with formation of the corresponding prolylethylamide, and with several variations substituting Phe or Ile for the tyrosyl in 5-position of the polypeptide, led to the formation of potent LRH agonists.

Another LRH agonist is disclosed in the copending U.S. patent application of McKinley and Sarantakis Ser. No. 472,269 which discloses [D-Lys$^6$]LRH prepared by solid phase methodology involving the following steps:

L-Pyroglutamyl-N$^{im}$-tosyl-L-histidyl-L-tryptophyl-O-benzyl-L-seryl-O-2,6-dichlorobenzyl-L-tyrosyl-N$^\epsilon$-2-chlorobenzyloxycarbonyl-D-lysyl-L-leucyl-N$^g$-tosyl-L-arginyl-L-prolyl-glycyl-benzhydrylamine resin Benzhydrylamine hydrochloride resin (Rivaille et al., Helv. Chim. Acta. 54, 2772 (1971) (3 g.) in a Merrifield

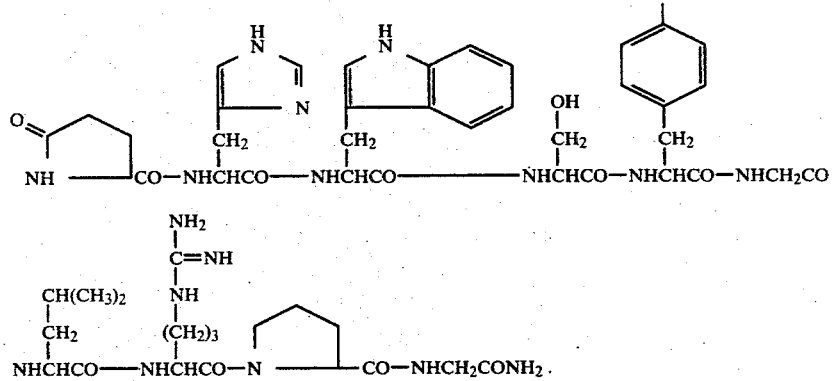

Chang et al. J. Med. Chem. 15, 623 (1972). LRH is endogenously produced by the hypothalamus and stimulates the secretion of the pituitary gonadotropins, luteinizing hormone and follicle stimulating hormone. LRH is presently employed clinically as a diagnostic and therapeutic agent for treatment of infertility by inducing ovulation and in other hypogonadotropic and hypogonadal disorders.

Recently, several LRH agonists have been synthesized. In 1972, Fujino et al., Biochem. Biophys. Res. Commun. 49, 863 reported that the nonapeptide des-Gly-NH$_2^{10}$-[Pro$^9$-ethylamide]LRH has five times the activity of LRH itself. Monahan et al., Biochemistry, 12, 4616 (1973), reports that replacement of the Gly$^6$ moiety in LRH by D-Ala$^6$ to form the decapeptide [D-Ala$^6$]LRH increased the potency of the parent hormone by from 350 to 450 percent. In 1974, Coy et al., Biochem. Biophys. Res. Commun. 57, 335, reported that the nonapeptide [D-Ala$^6$, des-Gly-NH$_2^{10}$]LRH ethylamide was markedly more potent than LRH and the previously known LRH agonists. In 1974, Fujino et al., Biochem. Biophys. Res. Comm. 57, 1248, reported that [Phe$^5$, D-Ala$^6$, des-Gly$^{10}$]LRH ethylamide possessed activity comparable to [D-Ala$^6$, des-Gly$^{10}$]LRH ethylamide in the order of 50 times that of LRH itself. Fujino et al. have also reported in Biochem. Biophys. Res. Comm. 60, 406(1974) that [Ile$^5$, D-Ala$^6$, des-Gly$^{10}$]LRH ethylamide provides intense activity as an ovulation-inducing LRF agonist; [DL-Leu$^6$]LRH and [DL-Leu$^6$, des-Gly$^{10}$]LRH ethylamide exhibited 8 and 20 times the ovulation inducing activity, respectively, of LRH and that an entire series of polypeptides, modified by substituting for the 6-amino acid of LRH, a D-ala, D-α-aminobutyric acid, D-norvaline, D-Leu, D-Phe or vessel is treated with trifluoroacetic acid (two times, for 5 minutes each), washed with methylene chloride (two times) and dimethylformamide (two times), neutralized with 15% triethylamine in dimethylformamide (two times, for 10 minutes each), and washed with methylene chloride (four times), methanol (three times), and methylene chloride, again (three times). A solution of t-butyloxycarbonyl-glycine (0.79 g., 4.5 m moles) in methylene chloride and dimethylformamide (10:1) is added to the vessel and shaken for 15 minutes. Diisopropylcarbodiimide (0.72 ml., 4.5 m moles) is then added, and the mixture shaken at ambient temperature for 5 hours. The reaction mixture is filtered, washed with methylene chloride, and the vessel recharged in the above manner with t-butyloxycarbonyl-glycine and diisopropylcarbodiimide. Twenty hours later, the reaction mixture is filtered, washed with methylene chloride, dimethylformamide, 15% triethylamine in diemthylformamide, dimethylformamide, methylene chloride (three times), methanol (two times), and methylene chloride (three times) and dried in vacuo. The resin is found to be substituted to the extent of 0.30 m moles of t-butyloxycarbonyl-glycine per gram of resin.

The following amino acid residues are introduced onto the above resin consecutively: t-butyloxycarbonyl-L-proline (4.5 m moles), t-butyloxycarbonyl-N$^g$-tosyl-L-arginine (2.3 m moles) and t-butyloxycarbonyl-L-leucine (2.3 m moles). The remainder of the synthesis is carried out using a Beckman 990 peptide synthesizer adding the following residues: t-butyloxycarbonyl-N$^\epsilon$-2-chlorobenzyloxycarbonyl-D-lysine (4.5 m moles), t-butyloxycarbonyl-O-2,6-dichlorobenzyl-L-tyrosine (4.5 m moles), t-butyloxycarbonyl-O-benzyl-L-serine (4.5 m moles), t-butyloxycarbonyl-L-tryptophan (4.5 m moles), t-butyloxycarbonyl-N$^{im}$-tosyl-L-histidine, (4.5 m moles), and L-pyroglutamic acid (4.5 m moles). All the couplings are carried out in a mixture of methylene chloride and dimethylformamide (3:1) at ambient temperature using a 10% excess of diisopropylcarbodiimide, which is added in two portions over a period of thirty minutes. A coupling time of eighteen hours is used for the additions done manually with the Merrifield vessel and a time of two hours is used with the automated synthesizer. Each coupling is then effected a second time using one half the original quantities of reactants and allowing a reaction time of two hours. The washings between couplings are the same as those described above after the coupling of t-butyloxycarbonyl-glycine. The deprotection and neutralization is carried out as follows: (a) 1:1 methylene chloride and trifluoroacetic acid containing 5% ethanedithiol (for a total time of thirty minutes); (b) methylene chloride; (c) dimethylformamide; (d) 15% triethylamine in dimethylformamide (two times for 10 minutes each); (e) dimethylformamide (two times); (f) methylene chloride (six times).

The washed resin is dried in vacuo overnight.

L-Pyroglutamyl-L-histidyl-L-tryptophyl-L-seryl-L-tyrosyl-D-lysyl-L-leucyl-L-arginyl-L-prolyl-glycinamide The product of the above described preparation is treated in vacuo with anhydrous liquid hydrogen fluoride (50 ml.) and anisole (10 ml.) at ambient temperature for forty minutes. The hydrogen fluoride is removed as quickly as possible under reduced pressure, and the residue extracted with diethyl ether. The remaining residue is extracted with 0.5 N acetic acid and lyophylized to leave the above titled product (1.44 g.).

Purification and characterization of L-pyroglutamyl-L-histidyl-L-tryptophyl-L-seryl-L-tyrosyl-D-lysyl-L-leucyl-L-arginyl-L-prolylglycinamide The crude [D-Lys$^6$]LRH is purified as follows: 1.44 g. of this product in 5 ml. of the upper phase of 1:1 mixture of n-butanol and 0.1 M ammonium acetate is applied to the top of a column (2.9 cm. in diameter and 100 cm. in height) with a bed of Sephadex G-25 F previously equilibrated with the upper phase of that system. The column is eluted with the upper phase and fractions of 4 ml. each are taken. The column effluent is monitored by use of the Folin-Lowry color reaction on every third fraction. Five peptide containing fractions are obtained, but they contain only 13% of the material applied to the column. Elution of the column with 0.5 N acetic acid produces three main peptide containing fractions: (I) 222 mg., (II) 621 mg., (III) 145 mg. Amino acid analysis and thin layer chromatography system BWAP (4:2:1:1) (n-butanol:water:acetic acid:pyridine) show fractions II and III (766 mg.) to contain the same major material. They are combined and applied in 3 ml. of 0.5 N acetic acid to a column (2.9 cm. in diameter and 100 cm. in height) of Sephadex G-15 previously equilibrated with 0.5 N acetic acid, and eluted with that solvent. Fractions of 2 ml. each are taken and monitored as described before. Five major fractions are obtained: (A) 117–115 (101 mg.), (B) 116–125 (100 mg.), (C) 126–133 (22 mg.), (D), 140–145 (30 mg.), (E) 146–155 (221 mg.). Fraction B is homogeneous by thin layer chromatography system BWAP (4:2:1:1) on silica gel (R$_f$0.37). Thin layer chromatograms are visualized by chlorine peptide reagent; $[\alpha]_D^{25} = -36.65$ (c 1.00%, 1% AcOH).

After hydrolysis of the peptide in 6 N HCl containing 4% thioglycolic acid for 20 hours at 110° C. in a closed system under nitrogen, the following values for the amino acid residues are obtained: Glu 0.97; His 0.92; Trp 0.73; Ser 0.78; Tyr 1.04; Lys 1.05; Leu 0.97; Arg 0.85; Pro 1.02; Gly 1.00.

Yet another LRH agonist is disclosed in the copending U.S. patent application of V. Garsky, Ser. No. 561,525, filed Mar. 24, 1975, entitled [2-methyl-Ala$^6$]LRH which discloses and claims [2-methyl-Ala$^6$]LRH prepared by solid phase methodology involving the following steps:

L-(5-oxoprolyl)-N$^{im}$-tosyl-L-histidyl-L-tryptophyl-O-benzyl-L-seryl-O-2,6-dichlorobenzyl-L-tyrosyl-2-methylalanyl-L-leucyl-N$^g$-tosyl-L-arginyl-L-prolyl-glycyl-benzhydrylamine resin Benzhydrylamine hydrochloride resin (10.0 g., 5.3 m moles) is placed in a Beckman 990 peptide synthesizer reaction vessel and treated in the following manner:

(1). methylene chloride (three times)
(2). 5 minute prewash with 1:1 trifluoroacetic acid-methylene chloride (v/v) containing 0.5% dithioerythritol
(3). 30 minute deprotection with the above described trifluoroacetic acid
(4). methylene chloride (six times)
(5). 15% triethylamine in dimethylformamide (three times)
(6). methylene chloride (six times)

A contact time of 1.5 minutes is allowed for each wash unless otherwise indicated.

The resin is gently stirred with t-butyloxycarbonyl glycine (5.6 g., 31.8 m moles in methylene chloride) and 35.0 ml. of 1 M diisopropylcarbodiimide (DIC) in methylene chloride (DIC added in two portions over 30 minutes). After stirring for 18 hours the peptide-resin is washed successively with methylene chloride (three times), dimethylformamide (three times) and methylene chloride (three times). Any unreacted sites are acylated with acetylimidazole (60 ml., 2.5% in methylene chloride) for 30 minutes and the resin washed with methylene chloride (six times).

The deprotection of the attached amino acid is carried out as described in steps (1) through (6) above.

The following amino acid residues are then introduced consecutively: t-butyloxycarbonyl-L-proline (6.8 g., 31.8 m moles in methylene chloride, 35 m moles DIC), t-butyloxycarbonyl-L-N$^g$-tosyl-L-arginine (11.2 g., 31.8 m moles in dimethylformamide, 35 m moles DIC), t-butyloxycarbonyl-L-leucine monohydrate (7.9 g., 31.8 m moles in methylene chloride, 35 m moles DIC), t-butyloxycarbonyl-α-aminoisobutyric acid (6.3 g., 31.8 m moles in methylene chloride, 35 m moles DIC); t-butyloxycarbonyl-O-2,6-dichlorobenzyl-L-tyrosine (15.0 g., 31.8 m moles in dimethylformamide, 35 m moles DIC), t-butyloxycarbonyl-O-benzyl-L-serine (9.4 g., 31.8 m moles in methylene chloride, 35 m moles DIC), t-butyloxycarbonyl-L-tryptophane (9.7 g., 31.8 m moles in dimethylformamide, 35 m moles DIC). Reaction time for each coupling is three hours. Following each coupling the peptide-resin is washed and acylated as described above. Removal of the α-amino protecting group at each step is performed as described for the deprotection of the t-butyloxycarbonyl-glycine-resin (steps 1–6). The washed octapeptide-resin is dried, weighed (16.6 g.) and the synthesis continued with 19% (3.2 g., 1.0 m moles) of the peptide-resin. The next amino acid added is t-butyloxycarbonyl-N$^{im}$-tosyl-L-histidine (2.5 g., 6 m moles in 50% methylene chloride-dimethylformamide, 7.2 m moles DIC) followed by L-2-pyrrolidone-5-carboxylic acid (1.0 g., 8 m moles in dimethylformamide, 9.6 m moles DIC). The washed decapeptide resin is dried in vacuo to yield 2.6 g.

L-(5-oxoprolyl)-L-histidyl-L-tryptophyl-L-seryl-L-tyrosyl-2-methylalanyl-L-leucyl-L-arginyl-L-prolyl-glycinamide acetate salt The above described preparation (2.6 g.) is treated in vacuo with anhydrous liquid hydrogen fluoride (70 ml.) and anisole (10 ml.) at 0° C. for 45 minutes. The hydrogen fluoride and anisole are removed under reduced pressure and the residue suspended in 50% acetic acid. After filtration the filtrate is extracted with hexane and the aqueous phase lyophilized to leave the above titled produce (0.95 g.).

Purification and characterization of L-(5-oxoprolyl)-L-histidyl-L-tryptophyl-L-seryl-L-tyrosyl-2-methylalanyl-L-leucyl-L-arginyl-L-prolyl-glycinamide acetate salt The above titled crude product is purified as follows: 0.95 g. of this product is dissolved in a minimum amount of 2 N acetic acid and applied to a column (2.9×100 cm) of Sephadex G-15 medium in 2 N acetic acid. The column is eluted with 2 N acetic acid and 2.5 ml. fractions collected. Tubes 120–130 are shown to be homogeneous by thin layer chromatography systems 4:1:5 (N-butanol:acetic acid:water) $R_f$0.30, and 7:7:6 (isoamyl alcohol:Pyridine:water) $R_f$0.60, on silica gel. Thin layer chromatograms are visualized with iodine and chlorine peptide reagent.

After hydrolysis of the peptide (6 N HCl, 4% thioglycolic acid) for 20 hours at 110° C. in a closed system under nitrogen, the following values for the product are obtained: Glu 0.96, His 0.95, Trp 0.85, Ser 0.66, Tyr 0.97, 2-Me-Ala 0.95, Leu 0.94, Arg 0.97, Pro 1.03, Gly 1.00.

Additional modifications of the basic LRH structural sequence resulting in LRH agonists of increased activity in comparison with LRH itself, involve the production of the following compounds by conventional preparatory techniques: [D-Lys$^6$, des-Gly-NH$_2$$^{10}$]LRH ethylamide, [D-Glu$^6$, des-Gly-NH$_2$$^{10}$]LRH ethylamide, [D-Asp$^6$, des-Gly-NH$_2$$^{10}$]LRH ethylamide, [D-Cys$^6$, des-Gly-NH$_2$$^{10}$]LRH ethylamide, [D-Cys$^6$, des-Gly-NH$_2$$^{10}$]LRH ethylamide, [D-Leu$^6$, L-Ser$^7$, des-Gly-NH$_2$$^{10}$]LRH ethylamide, [D-Leu$^6$, L-Cys$^7$, des-Gly-NH$_2$$^{10}$]LRH ethylamide, [D-Ala$^6$, L-Cys$^7$, des-Gly-NH$_2$$^{10}$]LRH ethylamide, and [D-Ser$^6$, L-Ser$^7$, des-Gly-NH$_2$$^{10}$]LRH ethylamide. These LRH agonists are in excess of 40 times as active as LRH itself, when evaluated as ovulation inducing agents as a result of induced LH production.

Thus, LRH and the LRH agonists disclosed supra present a family of polypeptides which may be depicted as:

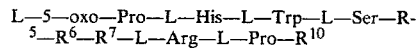

in which
R$^5$ is L-tyr, L-Phe or L-ILe;
R$^6$ is Gly, 2-methyl-Ala, DL-Leu, D-Ala, D-α-aminobutyroyl, D-norvaline, D-Leu, D-Phe, D-Ser, D-Lys, D-Glu, D-Asp or D-Cys;
R$^7$ is L-Leu, L-Cys or L-Ser;
and
R$^{10}$ is Gly or NHC$_2$H$_5$.

In general, the modifications of LRH involve (1) removal of the Gly$^{10}$ group with formation of a Pro ethylamide, (2) replacement of the Gly$^6$ group by an amino acid from the D-series, an optically inactive mixture (DL-Leu) or an optically inactive amino acid (2-methyl-Ala), (5) replacement of the Tyr$^5$ group by L-Phe or 6-Ile, and (4) replacement of the Leu$^7$ group by L-Ser or L-Cys. The first two modifications appear to be most significant, in relation to increased activity when compared to LRH itself.

LRH agonists, like LRH itself, have been used for diagnosis and treatment of infertility and hypogonadotropic and hypogonadal disorders. LRH and LRH agonists induce ovulation in various mammalian species, including man, presumably through stimulation of the pituitary-ovarian axis.

DESCRIPTION OF THE INVENTION

It has now been discovered, surprisingly, that the ovulation-inducing agents, LRH and LRH agonists, are very effective claudogenic and/or interceptive agents useful in preventing pregnancy by averting implantation or termination the development of an implanted fertilized ovum (blastocyst) in the placental mammal.

Thus, the process of this invention provides a method for preventing pregnancy in a placental mammal which comprises administering LRH or an LRH agonist to said mammal for a period of time and in an amount sufficient to prevent said pregnancy.

The luteinizing hormone releasing hormone, or an agonist thereof, may be employed as in a claudogenic or interceptive sense, in that ovulation may be induced in the mammal at a time prior to normal ovulation, coupled with continued administration of LRH or its agonist for a period sufficient to prevent the successful establishment of pregnancy. In the menstruating mammal, LRH or an agonist thereof, may be administered at approximately day 10 of any given menstrual cycle, assuming normal ovulation occurs later. Continued administration of LRH or the agonist over approximately a three day period following the day 10 induced ovulation assures rejection of the ovum in case of fertilization, the remainder of the postovulatory period of the menstrual cycle proceeding normally with no untoward effect. LRH or the LRH agonist is thereby used effectively to avoid pregnancy by disruption of the normal transport-implantation sequence of the fertilized ovum.

As understood, the presence of LRH or an LRH agonist effects hyperstimulation of the pituitary, effecting an abnormal secretion of LH resulting in over stimulation of the progesterone producing function of the corpus luteum which "misdates" or disrupts the physiological integrity of the endometrial tissue creating an incompatible site for acceptance or retention of the blastocyst.

The time period for administration of the claudogenic/interceptive agents of this invention in the human female may be ascertained by the initial detection of human chorionic gonadotropic (HCG) hormone in the blood serum. Administration of LRH or an LRH agonist would then be initiated and continued until the chorionic gonadotropin was no longer detectable. Or, LRH or an agonist thereof may be routinely administered, post coitally, to effect a claudogenic or interceptive disruption of the pregnancy.

Thus, the invention may be expressed as a method for preventing pregnancy in a menstruating mammal which comprises increasing the blood serum luteinizing hormone concentration of said mammal, post coitally, during the periovulatory or post-ovulatory (luteal) phase of the menstrual cycle, in an amount sufficient to effect a claudogenic or interceptive disposal of a fertilized ovum and re-establish the normal menstrual cycle. By "periovulatory" applicant means that period from about three days prior to ovulation up to and including the time of ovulation. Similarly, the method of this invention provides a technique for re-establishing a normal menstrual cycle in a placental mammal, during which cycle an unprotected sexual intercourse has occurred, which comprises post coitally administering LRH or an LRH agonist to said mammal for a period of time and in an amount sufficient to assure completion of the normal menstrual cycle by menses.

The blood serum luteinizing hormone (LH) concentration in a normal human female is generally at baseline concentration except at the time of the midcycle ovulatory LH surge, after which the serum LH values return to baseline concentrations. During pregnancy, the serum LH and HCG concentration generally rises. It is believed that an induced hypersecretion of LH to provide a serum concentration above that normally found during pregnancy for a period of at least three days and preferably for seven days, immediately following an unprotected intercourse, or for a period of from about five to about seven days during the luteal phase, and during that menstrual cycle in which an unprotected intercourse occurred, not immediately following the intercourse, is sufficient to prevent the successful transport or implantation of a fertilized ovum. Although treatment for a single day has been found to be effective in the standard test animal, the difficulties involved in determining that critical day for a given patient are too great when compared to the risks involved, to be considered a pragmatic approach to the problem at this time. Therefore, as a practical approach to the problem, a three day treatment period, immediately following an unprotected intercourse is considered minimal.

Thus, the present invention provides a method for preventing pregnancy in a placental mammal through inhibition of successful implantation of a fertilized ovum by increasing the blood serum luteinizing hormone concentration of said mammal, post coitum, and for a period of about 72 hours up to about 350 hours in the case of a menstruating mammal. Specifically, this invention involves a method for preventing successful implantation or disruption of an established implantation of a fertilized ovum in a placental mammal which comprises administering to said mammal, a daily dose of from about 5 to about 20 milligrams of LRH or an LRH agonist for a period of from about 3 to about 14 days, post coitum.

The LRH agonist property of a polypeptide is readily determined by the following in vivo test procedures:

(a) Testing for Gonadotropin (LH) Releasing Activity in Ovariectomized, Steroid Blocked Rats.

Mature female rats were bilaterally ovariectomized and used at least one month later (at least 5/group.) Seventy-two hours prior to use, the rats received 50 μg estradiol benzoate and 25 mg. progesterone, subcutaneously, in oil, in order to block the high endogenous release of pituitary gonadotropins that occurs as a consequence of castration. Such surgically and steroid-manipulated rats become equisitively sensitive to gonadotropin-releasing hormones. On the day of assay, a pre-injection blood sample is drawn from a jugular vein; the test material in then injected via the jugular vein and a second blood sample is obtained 20 minutes later. LH was determined by radioimmunoassay; a significant rise in serum LH levels attests to a compound's gonadotropin-releasing activity.

(b) Ovulation Induction in the Rat

Proestrous female rats were injected intraperitoneally with a hypnotic dose of Nembutal about (~60 mg/kg) at 1:30 P.M. This treatment blocks the spontaneous ovulatory surge of pituitary LH which generally occurs between 2:00 and 4:00 P.M. Between 1:40 and 1:50 P.M. the recipients then received the test material via the jugular vein. The following morning the animals are sacrificed and the fallopian tubes examined for ova under a dissecting microscope.

The method of this invention provides a simple, physiologically compatable technique for preventing undesired pregnancies which results in no known or recognizable adverse change in the patient, providing for immediate return to the normal fertility cycle during the cycle subsequent to the treatment, without adverse effects sometimes noted in steroidal hormone treatments employed in a planned contraceptive regimen.

LRH and the LRH analogues disclosed in this application where shown to be effective claudogenic/interceptive agents by testing them in the following in vivo procedure:

Female, Sprague-Dawley rats, 350±30 g., are caged daily (P.M.) with adult, sexually experienced Sprague-Dawley males. Vaginal smears are taken each A.M. after cohabitation. The presence of vaginal sperm is used as the index of mating and the initiation of pregnancy. Day 1 of pregnancy is taken as the day sperm is found in the vaginal smear. Mated females are then grouped separately. Treatment is begun at any time over the first 12 days of pregnancy at a divided dose (9 A.M. and 3 P.M.) or a single treatment. Claudogenic activity is defined for compounds administered over the first 7 days inclusive of pregnancy (Pre-implantation). Interceptive activity is defined for compounds administered days 7–12 inclusive of pregnancy (Post-implantation). Rats are sacrificed on day 14 (claudogen), day 18 (interceptive) or allowed to come to term prior to the option of sacrifice (claudogen or interceptive.) Rats containing at least one "Normal" fetus are considered pregnant.

For the purpose of defining the post-coital stages of pregnancy in the rat as an experimental model, the following schedule is provided in definition of post-coital contraceptive activity which, for the purpose of this disclosure, is intended to embrace both pre-(claudogenic) and post-(interceptive) implantation contraceptive activity: day 1—vaginal sperm; days 1–3—ova transport in oviducts, and fertilization; days 3–5 blastocyst free in uterine lumen; days 5–7—implantation into uterine wall; days>7—post implantation.

The results of the testing are presented in the following table in which SC means subcutaneous, PO means per os and terat. means teratogenic.

| Agent<br>No. of Rats<br>Route | Total<br>Daily<br>Dose<br>μg/Rat | Rx<br>Days<br>Post<br>Coitus | % inhi-<br>bition of<br>Pregnancy | |
|---|---|---|---|---|
| Oil - 10 - SC | — | 1-3 | 0 | |
| 65 - SC | — | 1-7 | 1.5 | |
| 20 - SC | — | 7-12 | 0 | |
| 4 - SC | — | 3 | 0 | |
| 15 - PO | — | 1-7 | 6.6 | |
| 3 - PO | — | 7-12 | 0 | |
| LRH - 5 - SC | 100 | 1-3 | 0 | |
| 5 - SC | 300 | 1-3 | 20 | |
| 5 - SC | 500 | 1-3 | 40 | |
| 5 - SC | 1000 | 1-3 | 40 | |
| 5 - SC | 50 | 1-7 | 0 | |
| 5 - SC | 100 | 1-7 | 100 | terat. |
| 5 - SC | 1000 | 1-7 | 100 | |
| 5 - PO | 500 | 1-7 | 20 | |
| 10 - PO | 1000 | 1-7 | 60 | |
| 4 - SC | 200 | 7-12 | 50 | |
| 5 - PO | 500 | 7-12 | 0 | |
| 5 - PO | 1000 | 7-12 | 100 | |
| 4 - SC | 5000 | 3 | 100 | terat. |
| [des-Gly—NH2[10], D-Ala[6]]LRH ethylamide | | | | |
| 5 - SC | 50 | 1-3 | 40 | |
| 5 - SC | 100 | 1-3 | 80 | |
| 5 - SC | 200 | 1-3 | 100 | |
| 4 - SC | .002 | 1-7 | 0 | |
| 10 - SC | .010 | 1-7 | 30 | |
| 6 - SC | 1.0 | 1-7 | 100 | |
| 5 - SC | 100 | 1-7 | 100 | |
| 15 - PO | 1000 | 1-7 | 100 | |
| 5 - SC | 0.10 | 7-12 | 0 | |
| 6 - SC | 1.0 | 7-12 | 100 | |
| 5 - SC | 5.0 | 7-12 | 100 | |
| 5 - PO | 200 | 7-12 | 0 | |
| 6 - PO | 500 | 7-12 | 67 | |
| 5 - PO | 1000 | 7-12 | 100 | |
| 5 - SC | 5000 | 3 | 100 | |
| 4 - SC | 5000 | 7 | 0 | |
| 5 - SC | 5000 | 8 | 100 | |
| [D-Lys[6]]LRH | | | | |
| 5 - SC | 100 | 1-3 | 0 | |
| 5 - SC | 300 | 1-3 | 60 | |
| 4 - SC | 300 | 1-7 | 100 | |
| 5 - PO | 500 | 1-7 | 40 | |
| 5 - SC | 5.0 | 1-12 | 20 | |
| [D-Ala[6]]LRH | | | | |
| 6 - SC | 100 | 1-3 | 17 | |
| 6 - SC | 300 | 1-3 | 50 | |
| [2-methyl-Ala[6]]LRH | | | | |
| 5 - SC | 100 | 1-7 | 75 | |
| 5 - SC | 500 | 1-7 | 100 | |
| [des-Gly—NH2[10], D-Leu[6]]LRH ethylamide | | | | |
| 5 - SC | 200 | 1-3 | 20 | |
| 10 - SC | 200 | 1-7 | 100 | |
| [des-Gly—NH2[10], D-α-aminobutyroyl[6]]LRH ethylamide | | | | |
| 5 - SC | 5.0 | 1-7 | 40 | |
| 4 - SC | 100 | 1-7 | 100 | |
| 5 - SC | 5.0 | 7-12 | 80 | |
| 5 - PO | 500 | 7-12 | 20 | |
| [des-Gly—NH2[10], α-aminobutyroyl[6]]LRH ethylamide | | | | |
| 5 - SC | 200 | 7-12 | 80 | |
| 6 - SC | 200 | 1-7 | 100 | |

Based upon the findings of activity in the prevention of development of pregnancy in the rat model and the fact that present evidence indicates that the hormonal situation relating to the reproductive cycle up to and including ovulation, is similar in many varied species of female placental mammals, e.g. the human reproductive cycle is physiologically analogous with that of the rat, the activities of the peptides of this invention effectively interferes with the development of the blastocyst pre- and post-implantation in the uterus in all placental mammals, including the human.

LRH and LRH agonists may be administered parenterally or orally in any convenient form, with or without conventional liquid or solid pharmaceutical adjuvants well known to the art. In addition, conventional adducts of the nonapeptide may be employed to prolong its effectiveness, such as the protamine zinc or aluminum adducts which are prepared by conventional techniques. Assimilation of the polypeptides upon oral administration may be improved, if desired, by supplying an enteric coating, etc.

LRH itself was shown by the preceding test procedure to be effective in inhibiting pregnancy when administered post-coitally to the rat, subcutaneously. LRH produces an anti-pregnancy effect when administered through days 1-3, days 1-7, days 7-12 or on day 3 alone. The post-coital anti-pregnancy effect can be manifested prior to uterine implantation (days 1-7; claudogenic effect) or after uterine implantation (after day 7; interceptive effect). It has been observed, where sacrifice occurred on day 14 of pregnancy prior to term, that some signs of teratogenicity attends the use of LRH under certain dosing regimens. Therefore, LRH cannot at this time, be considered suitable for use in the human, unless very close controls are employed to assure contraception, although its use in domestic animals, were the termination of an undesired pregnancy is the sole consideration, as with thoroughbred mares, purebred dogs, cats, ewes, does, etc., LRH is quite acceptable. The LRH agonists have demonstrated no indication of teratogenic properties in any study completed to date and are therefore quite acceptable for human use.

The appropriate administrative dose is determinable, for any LRH agonist, based upon its activity relative to LRH. A subjective determination by the physician for each individual patient is determinative of the appropriateness of the dosage regimen, as evidenced by blood serum analysis, expulsion of the ovum and ultimately menses.

For administration to the human patient, the LRH agonists may be effectively employed in a dose range of from about 5 to 20 milligrams per day, orally or parenterally, in the following frequency regimens:

1. 1-2 times per day per female, for 7-10 days post-coitum, beginning immediately following an unprotected intercourse if it occurred at time of anticipated fertile (ovulatory) period during the menstrual cycle.

2. 1-2 times per day female, from days 21 through 28 of the menstrual cycle, inclusive, if unprotected intercourse has occurred at time of anticipated fertile period.

3. 1-2 times per day per female on a routine monthly basis from days 14 through 28 of each menstrual cycle, inclusive, whether or not an unprotected intercourse during the anticipated fertile period has occurred.

4. 1-2 times per day per female on a routine monthly basis from days 21 through 28 of each menstrual cycle inclusive whether or not an unprotected intercourse during the anticipated fertile period has occurred.

If treatment is twice per day, the compound is given once in A.M. and once in P.M. 9 hours apart.

In veterinary practice, the claudogenic/interceptive agent (LRH or an LRH agonist) is administered orally or parenterally for a period of time related to the animal's estrous cycle to terminate pregnancy by preventing successful development or implantation of the blastocyst. A 5 to 10 milligram daily dose is suitable for a dog or cat while a proportionately increased dosage may be used on larger animals, such as the horse.

As an anti-littering agent, LRH and LRH agonists are useful in the control of rodent populations through constant supply feed stations without the use of conventional rodenticides and their attendent danger to other animals in the environment. In addition, LRH and LRH agonists may be used to terminate undesired or unplanned pregnancies in prize domestic animals such as the thoroughbred mare, purebred bitch, ewe or doe, as well as the family cat.

What is claimed is:

1. A method for preventing pregnancy in a menstruating mammal which comprises administering luteinizing hormone releasing hormone or an agonist thereof to said mammal for from three to about fourteen days, during the period extending from about three days prior to ovulation to the time of normal menses, in an amount sufficient to inhibit or terminate implantation of a fertilized ovum.

2. A method for terminating pregnancy in a human which comprises administering luteinizing releasing hormone or an agonist thereof to said human, upon detection of human chorionic gonadotropic hormone in the blood serum of said human, in an amount and for a period of time sufficient to terminate said pregnancy.

3. A method for preventing pregnancy in a menstruating mammal which comprises increasing the blood serum luteinizing hormone concentration during the postovulatory phase of said menstrual cycle in an amount sufficient to inhibit or terminate implantation of a fertilized ovum.

4. The method of claim 3 in which the increase of blood serum luteinizing hormone is induced by administration of LRH or an LRH agonist.

5. A method for terminating pregnancy in a menstruating mammal which comprises administering daily to said mammal, post coitally, from about 5 to 20 milligrams of luteinizing hormone releasing hormone or an agonist thereof, for a period of from about 3 to about 14 days.

6. The method of claim 5 in which a luteinizing hormone releasing hormone agonist is administered to said menstruating mammal in an amount of from about 2.5 to 7.5 milligrams, twice per day.

7. A method for preventing pregnancy in a non-menstruating placental mammal which comprises administering LRH or an LRH agonist, post coitally, to said mammal for a period of time and in an amount sufficient to prevent said pregnancy.

8. A method for re-establishing a normal menstrual cycle in a placental mammal, said cycle having been interrupted by an unprotected intercourse, which comprises post coitally administering luteinizing hormone releasing hormone or an agonist thereof to said mammal in an amount sufficient to normally conclude said menstrual cycle by menses.

9. A method of claim 8 in which said unprotected intercourse produced a fertilized ovum and a pregnant state.

10. A method for maintaining a normal menstrual cycle in a placental mammal, during which cycle an unprotected intercourse has occurred, which comprises post coitally administering luteinizing hormone releasing hormone or an agonist thereof to said mammal in an amount sufficient to normally conclude said menstrual cycle by menses.

11. A process for preventing reproduction consisting essentially in administering to a female, warm-blooded animal in the reproductive age, an effective dose of a nonapeptide L-pGlu-L-His-L-Trp-L-Ser-L-Tyr-X-L-Leu-L-Arg-L-Pro-NH-C$_2$H$_5$ wherein X denotes the divalent, optically active D-form of phenylalanine for at least one day in the period after ovulation occurred.

12. The process of claim 11 wherein said nonapeptide is given as a single parenteral dose.

13. The process of claim 11 wherein said dose is administered orally.

14. An oral composition for preventing reproduction in warm-blooded female animals containing the nonapeptide L-pGlu-L-His-L-Trp-L-Tyr-X-L-Leu-L-Arg-L-Pro-NH-C$_2$H$_5$ wherein X denotes the divalent, optically active D-form of phenylalanine together with a pharmaceutically acceptable carrier.

15. The process for preventing reproduction consisting essentially in administering to a female, warm blooded animal in the reproductive age, an effective amount of a nonapeptide L-p-Glu-L-His-L-Trp-L-Ser-L-Tyr-X-L-Leu-L-Arg-L-Pro-NH-R wherein X denotes the optically active D-form of an amino acid of the formula -NH-CHR$^1$-CO- with R$^1$ being methyl and wherein R is ethyl for at least one day in the period after ovulation has occurred.

16. A method for terminating pregnancy in a menstruating mammal which comprises administering daily to said mammal, post coitally, from about 5 to 20 milligrams of a polypeptide of the formula:

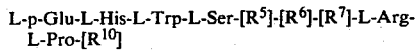

in which
R$^5$ is L-Tyr, L-Phe or L-Ile;
R$^6$ is Gly, D-Ala, DL-Leu, 2-methyl-Ala, D-α-aminobutyroyl, D-norvaline, D-Leu, P-Phe, D-Ser, D-Lys, D-Glu, D-Asp or D-Cys;
R$^7$ is L-Leu, L-Cys or L-Ser;
and
R$^{10}$ is Gly-NH$_2$ or -NHC$_2$H$_5$.

17. The method of claim 16 in which said polypeptide is [des-Gly-NH$_2^{10}$, D-Ala$^6$] LH-RH ethylamide.

18. The method of claim 16 in which said polypeptide is [D-Lys$^6$]LH-RH.

19. The method of claim 16 in which said polypeptide is [D-Ala$^6$[LH-RH.

20. The method of claim 16 in which said polypeptide is [2-methyl-Ala$^6$]LH-RH.

21. The method of claim 16 in which said polypeptide is [des-Gly-NH$_2^{10}$, D-Leu$^6$]LH-RH ethylamide.

22. The method of claim 16 in which said polypeptide is [des-Gly-NH$_2^{10}$, D-α-aminobutyroyl$^6$]LH-RH ethylamide.

23. The method of claim 16 in which said polypeptide is [des-Gly-NH$_2^{10}$, α-aminoisobutyroyl$^6$]LH-RH ethylamide.

24. A method for preventing pregnancy in a non-menstruating placental mammal which comprises administering a compound selected from the group consisting of [des-Gly-NH$_2^{10}$, D-Ala$^6$ LH-RH ethylamide, [D-Lys$^6$]LH-RH, [D-Ala$^6$]LH-RH, [2-methyl-Ala$^6$]LH-RH, [des-Gly-NH$_2^{10}$, D-Leu$^6$]LH-RH ethylamide, [des-Gly-NH$_2^{10}$, D-α-aminobutyroyl$^6$]LH-RH ethylamide and [des-Gly-NH$_2^{10}$, α-aminoisobutyroyl$^6$]LH-RH ethylamide, post coitally, to said mammal for a period of time and in an amount sufficient to prevent said pregnancy.